(12) United States Patent
Wood et al.

(10) Patent No.: US 6,261,785 B1
(45) Date of Patent: Jul. 17, 2001

(54) AMPLIFICATION AND DETECTION OF BORDETELLA PERTUSSIS

(75) Inventors: Janet L. Wood, Perryville; Tobin J. Hellyer, Owings Mills, both of MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 09/626,855

(22) Filed: Jul. 27, 2000

(51) Int. Cl.$^7$ .............................. C12Q 1/68; C12P 19/34; C07H 21/04; C12N 15/00

(52) U.S. Cl. ......................... 435/6; 435/91.2; 435/91.1; 536/22.1; 536/24.32; 536/24.33; 536/25.32; 935/77; 935/78

(58) Field of Search ................................ 536/22.1, 24.32, 536/24.33, 25.32, 24.2; 435/6, 91.2, 91.1; 935/77, 78

(56) References Cited

U.S. PATENT DOCUMENTS

| | | | |
|---|---|---|---|
| 5,492,811 | 2/1996 | Gilson et al. | 435/6 |
| 5,523,217 | 6/1996 | Lupski et al. | 435/9 |
| 5,863,721 | 1/1999 | Gilson et al. | 435/6 |
| 5,945,282 | 8/1999 | Rossau et al. | 435/6 |
| 5,994,066 | 11/1999 | Bergeron et al. | 435/6 |
| 6,017,711 | 1/2000 | Gilson et al. | 435/6 |
| 6,025,132 | 2/2000 | Jannes et al. | 435/6 |

FOREIGN PATENT DOCUMENTS

| | | | |
|---|---|---|---|
| 0 307 270 A1 | 3/1989 | (EP) | C12Q/1/68 |
| 0 307 270 B1 | 3/1989 | (EP) | C12Q/1/68 |

OTHER PUBLICATIONS

Weiss, et al. "Pertussis Toxin and Extracytoplasmic Adenylate Cyclase as Virulence Factors of *Bordetella pertussis*" *J. Infect. Dis.*, 150:219–222 (1984).

C. Locht, et al. "Pertussis Toxin Gene: Nucleotide Sequence and Genetic Organization" *Science*, 232:1258–1264 (1986).

M. Müller, et al. "Laboratory Diagnosis of Pertussis: State of the Art in 1997" *J. Clin. Microbiol.* 35, 10:2435–2443 (1997).

D. Furuya, et al. "Simultaneous Amplification of Bordetella Repeated Insertion Sequences and Toxin Promoter Region Gene by Polymerase Chain Reaction" *Immunopharmacol. Immunotoxicol.* 21(1):55–63 (1999).

D. Farrell, et al. "A Polymerase Chain Reaction (PCR) Method That Fulfills All of the Consensus Recommendations for the Use of PCR in the Diagnosis of *Bordetella pertussis* Infections" Abstr. No. 1569. p. 225. 39$^{th}$ ICAAC Meet. (1999).

T. Ross, et al. "Development and Clinical Evaluation of a PCR–based Assay for the Detection of *Bordetella pertussis* (BP) in Respiratory Specimens" Abstr. No. C–175. p. 170. 100$^{th}$ Gen. Meet. Am. Soc. Microbiol. (2000).

U. Heininger, et al. "Clinical Validation of a Polymerase Chain Reaction Assay for the Diagnosis of Pertussis by Comparison With Serology, Culture, and Symptoms During a Large Pertussis Vaccine Efficacy Trial" *Pediatrics* 105(3):E31 (2000).

*Primary Examiner*—W. Gary Jones
*Assistant Examiner*—J. Tung
(74) *Attorney, Agent, or Firm*—David W. Highet (57) ABSTRACT

Amplification primers and methods for specific amplification and detection of a pertussis toxin promoter target are disclosed. The primer-target binding sequences are useful for amplification and detection of *Bordetella pertussis* target in a variety of amplification and detection reactions.

30 Claims, 1 Drawing Sheet

FIG. 1

AMPLIFICATION AND DETECTION OF BORDETELLA PERTUSSIS

FIELD OF THE INVENTION

The present invention relates to methods for determining the presence or absence of *Bordetella pertussis* from respiratory samples or other patient specimens, cultures, or environmental samples. The method involves using nucleic acid primers to amplify specifically a pertussis toxin promoter (ptx) target, preferably using one of the techniques of Strand Displacement Amplification (SDA), thermophilic Strand Displacement Amplification (tSDA) or fluorescent real time tSDA.

BACKGROUND OF THE INVENTION

*B. pertussis* causes whooping cough (pertussis) in humans. Of the several toxins produced by *B. pertussis*, the pertussis toxin constitutes the main virulence factor as described by A. Weiss, et al. (1984. *J. infect. Dis.*, 150:219–222). Although other members of the genus Bordetellae (*B. parapertussis, B. bronchiseptica*) contain the pertussis toxin operon, the toxin is not expressed in these species due to mutations in the promoter region (C. Locht, et al., 1986, *Science*, 232:1258–1264). With appropriate primer design, these mutations confer specificity to the amplification and detection of *B. pertussis* DNA.

Nucleic acid amplification is a powerful technology, which allows rapid detection of specific target sequences. It is therefore a promising technology for the rapid detection and identification of *B. pertussis*. Examples of identification of *B. pertussis* using PCR to amplify a variety of genes including sequences of the pertussis toxin promoter gene were reviewed by M. Müller, et al. (1997. *Clin. Microbiol.* 35, 10:2435–3443). Other examples of the specific identification of *B. pertussis* using PCR to amplify sequences within the pertussis toxin promoter gene were described by D. Furuya, et al. (1999. *Immunopharmacol. Immunotoxicol.* 21(1):55–63), D. Farrell, et al. (1999. Abstr. No. 1569. pg. 225. 39$^{th}$ ICAAC Meet.), T. Ross, et al. (2000. Abstr. No. C-175 pg. 170 100$^{th}$ Gen. Meet. Am. Soc. Microbiol), and U. Heininger, et al. (2000. *Pediatrics* 105(3):E31). The oligonucleotide primers of the present invention are applicable to nucleic acid amplification and detection of *B. pertussis*.

The following terms are defined herein as follows:

An amplification primer is a primer for amplification of a target sequence by extension of the primer after hybridization to the target sequence. Amplification primers are typically about 10–75 nucleotides in length, preferably about 15–50 nucleotides in length. The total length of an amplification primer for SDA is typically about 25–50 nucleotides. The 3' end of an SDA amplification primer (the target binding sequence) hybridizes at the 3' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. *Proc. Natl. Acad. Sci. USA* 89:392–396 and 1992 *Nucl. Acids Res.* 20:1691–1696). The nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The tail is typically about 10–25 nucleotides in length. Its length and sequence are generally not critical and can be routinely selected and modified. As the target binding sequence is the portion of a primer which determines its target-specificity, for amplification methods which do not require specialized sequences at the ends of the target the amplification primer generally consists essentially of only the target binding sequence. For example, amplification of a target sequence according to the invention using the Polymerase Chain Reaction (PCR) will employ amplification primers consisting of the target binding sequences of the amplification primers described herein. For amplification methods that require specialized sequences appended to the target other than the nickable restriction endonuclease recognition site and the tail of SDA (e.g., an RNA polymerase promoter for Self-Sustained Sequence Replication (3SR), Nucleic Acid Sequence-Based Amplification (NASBA) or the Transcription-Based Amplification System (TAS)), the required specialized sequence may be linked to the target binding sequence using routine methods for preparation of oligonucleotides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified, the complementary second strand of the original nucleic acid sequence to be amplified and either strand of a copy of the original sequence which is produced by the amplification reaction. These copies serve as amplifiable targets by virtue of the fact that they contain copies of the sequence to which the amplification primers hybridize.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term species-specific refers to detection, amplification or oligonucleotide hybridization to a species of organism or a group of related species without substantial detection, amplification or oligonucleotide hybridization to other species of the same genus or species of a different genus.

The term assay probe refers to any oligonucleotide used to facilitate detection or identification of a nucleic acid. Detector probes, detector primers, capture probes, signal primers and reporter probes as described below are examples of assay probes.

A signal primer comprises a 3' target binding sequence which hybridizes to a complementary sequence in the target and further comprises a 5' tail sequence which is not complementary to the target (the adapter sequence). The adapter sequence is an indirectly detectable marker selected such that its complementary sequence will hybridize to the 3' end of the reporter probe described below. The signal primer hybridizes to the target sequence at least partially downstream of the hybridization site of an amplification primer. The signal primer is extended by the polymerase in a manner similar to extension of the amplification primers. Extension of the amplification primer displaces the extension product of the signal primer in a target amplification-dependent manner, producing a single-stranded product comprising a 5' adapter sequence, a downstream target binding sequence and a 3' binding sequence specific for hybridization to a flanking SDA amplification primer. Hybridization and extension of this flanking amplification primer and its subsequent nicking and extension creates amplification products containing the complement of the adapter sequence which may be detected as an indication of target amplification.

A reporter probe according to the present invention functions as a detector oligonucleotide and comprises a label which is preferably at least one donor/quencher dye pair, i.e., a fluorescent donor dye and a quencher for the donor fluorophore. The label is linked to a sequence or structure in the reporter probe (the reporter moiety) which does not hybridize directly to the target sequence. The sequence of the reporter probe 3' to the reporter moiety is selected to hybridize to the complement of the signal primer adapter sequence. In general, the 3' end of the reporter probe does not contain sequences with any significant complementarity to the target sequence. If the amplification products containing the complement of the adapter sequence described above are present, they can then hybridize to the 3' end of the reporter probe. Priming and extension from the 3' end of the adapter complement sequence allows the formation of the reporter moiety complement. This formation renders the reporter moiety double-stranded, thereby allowing the label of the reporter probe to be detected and indicating the presence of or the amplification of the target.

The term amplicon refers to the product of the amplification reaction generated through the extension of either or both of a pair of amplification primers. An amplicon may contain exponentially amplified nucleic acids if both primers utilized hybridize to a target sequence. Alternatively, amplicons may be generated by linear amplification if one of the primers utilized does not hybridize to the target sequence. Thus, this term is used generically herein and does not imply the presence of exponentially amplified nucleic acids.

SUMMARY OF THE INVENTION

The present invention provides oligonucleotide primers that can be used for amplification of a target sequence found in *B. pertussis*. More specifically, the target sequence comprises segments of the promoter for the pertussis toxin gene. The amplification primers have been designed for high-efficiency, high-specificity amplification at elevated temperatures, such as in tSDA and the PCR, however, they are also useful in lower-temperature amplification reactions such as conventional SDA, 3SR, TAS or NASBA. An oligonucleotide reporter probe that hybridizes to the complement of target specific signal primers is used to indirectly detect the amplification products.

The oligonucleotides of the invention may be used after culture as a means for confirming the identity of the cultured organism. Alternatively, they may be used with respiratory or other clinical samples or environmental samples for detection and identification of *B. pertussis* nucleic acid using known amplification methods. In either case, the inventive oligonucleotides and assay methods provide a means for rapidly discriminating between *B. pertussis* and other microorganisms, allowing the practitioner to identify this microorganism rapidly without resorting to the more traditional procedures customarily relied upon. Such rapid identification of the specific etiological agent involved in an infection provides information that can be used to determine appropriate action within a short period of time.

SUMMARY OF THE SEQUENCES

SEQ ID NO:1 is the sequence of an oligonucleotide used as an upstream primer for amplification of the pertussis toxin promoter region. SEQ ID NOs:2–3 are sequences of oligonucleotides used as downstreams primers for amplification of the pertussis toxin promoter region. SEQ ID NO:4 is the sequence of an oligonucleotide used as an upstream bumper for SDA amplification. SEQ ID NOs:5–6 are the sequences of oligonucleotides used as downstream bumpers for SDA amplification. SEQ ID NOs:7–10 are sequences of signal primers for amplification and detection of the pertussis toxin promoter region. SEQ ID NO:11 is a sequence for a reporter probe designed for detection of the pertussis toxin promoter region when used in conjunction with any of the aforementioned signal primers.

BRIEF DESCRIPTION OF THE DRAWINGS

The various objects, advantages and novel features of the present invention will be readily understood from the following detailed description when read in conjunction with the appended drawings in which:

FIG. 1 illustrates detection of a *B. pertussis* nucleic acid ptx target sequence in a Strand Displacement Amplification (SDA) reaction according to the method of the invention.

DETAILED DESCRIPTION OF THE INVENTION

The present invention relates to oligonucleotides, amplification primers and signal primers which exhibit specificity for *B. pertussis* in nucleic acid amplification reactions. Also provided are methods for detecting and identifying *B. pertussis* nucleic acids using the oligonucleotides of the invention. The preferred methods are to use SDA, tSDA or homogeneous real time fluorescent tSDA. These methods are known to those skilled in the art from references such as U.S. Pat. No. 5,547,861, U.S. Pat. No. 5,648,211, U.S. Pat. No. 5,846,726, U.S. Pat. No. 5,928,869, U.S. Pat. No. 5,958,700, U.S. Pat. No. 5,935,791, U.S. Pat. No. 6,054,279, U.S. patent application Ser. No. 09/590,061, filed Jun. 8, 2000, and U.S. patent application Ser. No. 09/602,996, filed Jun. 23, 2000, the disclosures of which are hereby specifically incorporated herein by reference. The primers of the present invention were designed based on an analysis of sequence data for the promoter of the pertussis toxin gene from multiple sources that were aligned to identify pertussis toxin promoter-specific regions. Primers developed for use in tSDA are shown in Table 1. Also shown are signal primers and a reporter probe for the amplification and detection of the resultant amplicons. The exemplary restriction endonuclease recognition sites (BsoBI) in the amplification primers are shown in boldface type and the target binding sequences are italicized. The target binding sequence of an amplification primer determines its target specificity.

TABLE 1

| Amplification Oligonucleotides | |
|---|---|
| <u>Upstream Primer</u> | |
| ptxL9: 5'-CGATTCC6CTCCAGACTTCTCGGG*CCGCATACGTGTTG* | (SEQ ID 1) |
| <u>Downstream Primers</u> | |
| ptxR10: 5'-ACCGCATCGATTGCATGTCTCGGG*TGCCGTGTTGGATTG* | (SEQ ID 2) |
| ptxR11: 5'-ACCGCATCGATTGCATGTCTCGGG*CGCCGTGTTGGATTG* | (SEQ ID 3) |
| <u>Upstream Bumper</u> | |
| ptxLB2: 5'-CGGCCGGCACCAT | (SEQ ID 4) |
| <u>Downstream Bumpers</u> | |
| ptxRB3: 5'-CGAAGGAGCGTTCA | (SEQ ID 5) |
| ptxRB4: 5'-ACCATCGCGCGACT | (SEQ ID 6) |
| <u>Signal Primers</u> | |
| ptxA1: 5'-ACGTTAGCCACCATACGGAT*CGTCGTACTAAACCCTCGATTCTTC* | (SEQ ID 7) |
| ptxA3: 5'-ACGTTAGCCACCATACGGAT*GATTCGTCGTACTAAACCCTCGATT* | (SEQ ID 8) |
| ptxA4: 5'-ACGTTAGCCACCATACGGAT*GATTCGTCGTACAAAACCCTCGATT* | (SEQ ID 9) |
| ptxA5: 5'-ACGTTAGCCACCATACGGAT*CTGCAGATGCGTCGTACAAAACCCTCGATT* | (SEQ ID 10) |
| <u>Reporter Probe</u> | |
| TBD10: 5'-(dabcyl)TAGTGCCCGAGCACT(rhodamine)ACGTTAGCCACCATACGGAT | (SEQ ID NO:11) |

As nucleic acids do not require complete complementarity in order to hybridize, it is to be understood that the probe and primer sequences herein disclosed may be modified to some extent without loss of utility as pertussis toxin promoter-specific probes and primers. As is known in the art, hybridization of complementary and partially complementary nucleic acid sequences may be obtained by adjustment of the hybridization conditions to increase or decrease stringency (i.e., adjustment of hybridization pH, temperature or salt content of the buffer). Such minor modifications of the disclosed sequences and any necessary adjustments of hybridization conditions to maintain *B. pertussis*-specificity require only routine experimentation and are within the ordinary skill in the art.

The amplification products generated using the primers disclosed herein may be detected by a characteristic size, for example, on polyacrylamide or agarose gels stained with ethidium bromide. Alternatively, amplified target sequences may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al. (1992, *Nucl. Acids Res.* 20:1691–1696) (a detector primer) or by hybridization, extension and conversion to double stranded form as described in EP 0 678 582 (a signal primer).

Figure 1:
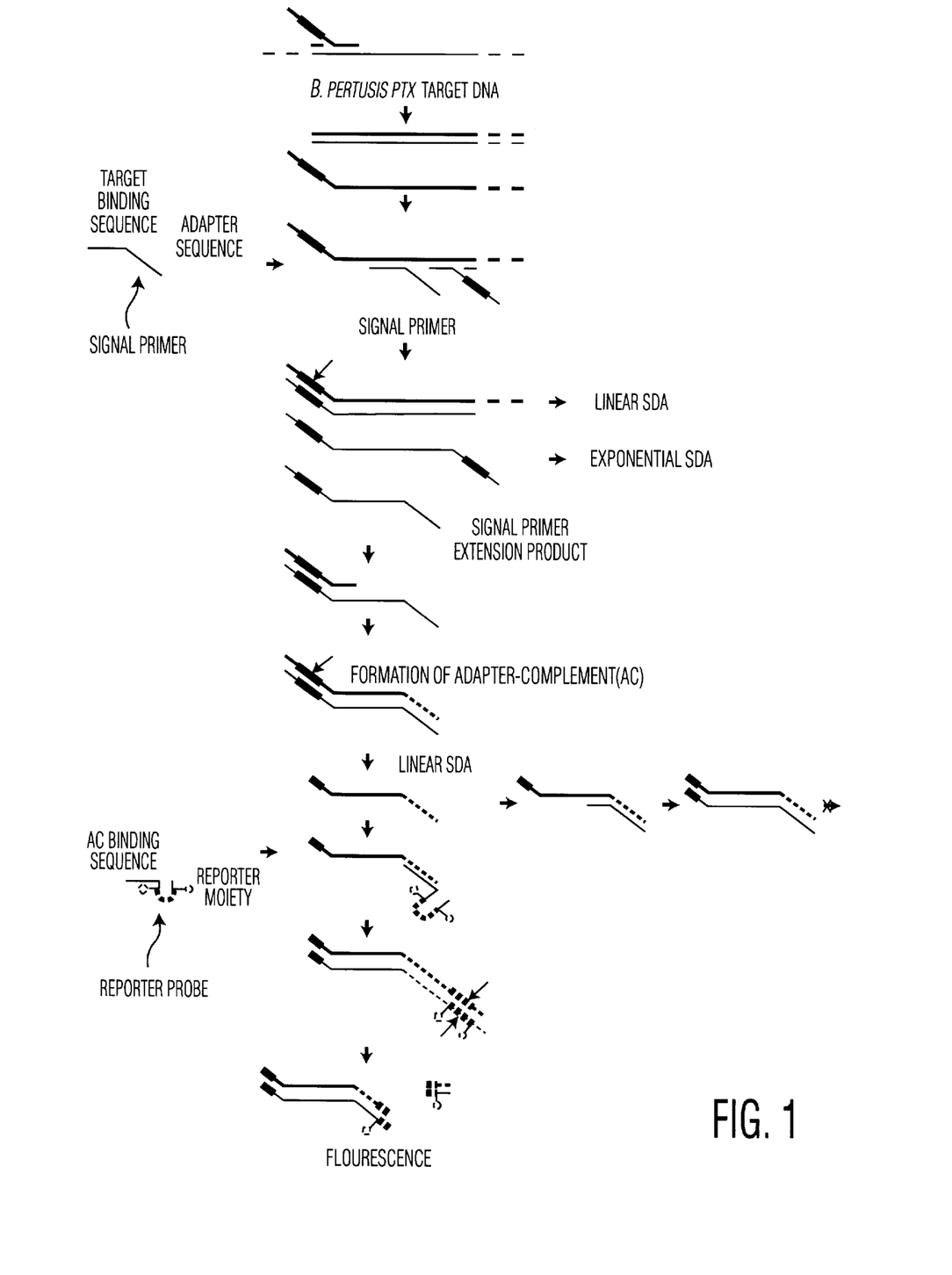

A preferred embodiment for the detection of amplified target is illustrated schematically in FIG. 1. In this embodiment, the 5' tail sequence of the signal primer is comprised of a sequence which does not hybridize to the target (the adapter sequence). The adapter sequence is an indirectly detectable marker which may be selected such that it is the same in a variety of signal primers which have different 3' target binding sequences (i.e., a "universal" 5' tail sequence). SEQ ID NOs:7–10 are particularly useful as signal primers, in conjunction with the amplification primers of the invention for detection of *B. pertussis*. Preferably, an assay probe is a single reporter probe sequence which hybridizes to the adapter sequence complement of the signal primers of the invention. SEQ ID NO:11 is particularly useful as a reporter probe when used in conjunction with the signal primers of the invention for detection of *B. pertussis*. Alternatively, an assay probe can be selected to hybridize to a sequence in the target that is between the amplification primers. In a further embodiment, an amplification primer or the target binding sequence thereof may be used as the assay probe.

The detectable label of the assay probe is a moiety which can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label that requires additional reagents to render it detectable. Indirectly detectable labels include, for example, chemiluminescent agents, enzymes that produce visible reaction products and ligands (e.g., haptens, antibodies or antigens) which may be detected by binding to labeled specific binding partners (e.g., antibodies or antigens/haptens). Ligands are also useful for immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a streptavidin-coated microtiter plate by means of the capture probe, and the chemiluminescent signal is developed and read in a luminometer. As another alternative for detection of amplification products, a signal primer as described in EP 0 678 582 may be included in the SDA reaction. In yet another alternative for detection of amplification products, the signal primer may contain sequences which do not hybridize to the target sequence, i.e., the adapter sequence. In this embodiment, as illustrated in FIG. 1, a reporter probe with associated label can hybridize to the complement of the adapter sequence. In both embodiments of the signal primer, secondary amplification products are generated during SDA in a target amplification-dependent manner and may be detected as an indication of target amplification.

For commercial convenience, amplification primers for specific detection and identification of nucleic acids may be packaged in the form of a kit. Typically, such a kit contains at least one pair of amplification primers. Reagents for performing a nucleic acid amplification reaction may also be included with the target-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., an oligonucleotide tagged with a label suitable for use as an assay probe, and/or reagents or means for detecting the label.

For the present invention, such a kit may be configured in order to provide the necessary components for a respiratory panel of organisms. Such a respiratory panel may include *B. pertussis, Legionella pneumophila, Mycoplasma pneumoniae* and *chlamydial* organisms in addition to other microorganisms capable of causing respiratory infection. Thus, such a respiratory kit would include the primers for amplification of a nucleic acid sequence specific for each of the organisms of the respiratory panel. Useful primers, bumpers, signal primers and reporter probes for amplifying and detecting *L. pneumophila* and *M. pneumoniae* are described in co-pending U.S. patent application Ser. No. 09/625,354, and co-pending U.S. patent application Ser. No. 09/626,355, respectively, the disclosures of which are specifically incorporated herein by reference. When used, such a respiratory panel kit may permit separate amplification reactions for each organism or one or more multiplex amplification reactions to provide results indicating the presence or absence of each of the organisms of the panel.

The target binding sequences of the amplification primers confer species hybridization specificity on the oligonucleotides and therefore provide species specificity to the amplification reaction. Thus, the target binding sequences of the amplification primers of the invention are also useful in other nucleic acid amplification protocols such as the PCR, conventional SDA (a reaction scheme which is essentially the same as that of tSDA but conducted at lower temperatures using mesophilic enzymes), 3SR, NASBA and TAS. Specifically, any amplification protocol which utilizes cyclic, specific hybridization of primers to the target sequence, extension of the primers using the target sequence as a template and separation or displacement of the extension products from the target sequence may employ the target binding sequences of the invention. For amplification methods that do not require specialized, non-target binding sequences (e.g., PCR), the amplification primers may consist only of the target binding sequences of the amplification primers listed in Table 1.

Other sequences, as required for performance of a selected amplification reaction, may optionally be added to the target binding sequences disclosed herein without altering the species specificity of the oligonucleotide. By way of example, the specific amplification primers may contain a recognition site for the restriction endonuclease BsoBI which is nicked during the SDA reaction. It will be apparent to one skilled in the art that other nickable restriction endonuclease recognition sites may be substituted for the BsoBI recognition site including, but not limited to, those recognition sites disclosed in EP 0 684 315. Preferably, the recognition site is for a thermophilic restriction endonuclease so that the amplification reaction may be performed under the conditions of tSDA. Similarly, the tail sequence of the amplification primer (5' to the restriction endonuclease recognition site) is generally not critical, although the restriction site used for SDA and sequences which will hybridize either to their own target binding sequence or to the other primers should be avoided. Some amplification primers for SDA therefore consist of 3' target binding sequences, a nickable restriction endonuclease recognition site 5' to the target binding sequence and a tail sequence about 10–25 nucleotides in length 5' to the restriction endonuclease recognition site. The nickable restriction endonuclease recognition site and the tail sequence are sequences required for the SDA reaction. As described in U.S. patent application Ser. No. 09/573,242, filed May 18, 2000, some amplification primers for SDA can consist of target specific sequences both 5' and 3' of the restriction enzyme recognition site. An increase in the efficiency of target specific hybridization can be attained with this design. For other amplification reactions (e.g., 3SR, NASBA and TAS), the amplification primers may consist of the target binding sequence and additional sequences required for the selected amplification reaction (e.g., sequences required for SDA as described above or a promoter recognized by RNA polymerase for 3SR). Adaptation of the target binding sequences of the invention to amplification methods other than SDA employs routine methods for preparation of amplification primers, such as chemical synthesis, and the well known structural requirements for the primers of the selected amplification reaction. The target binding sequences of the invention may therefore be readily adapted to *B. pertussis*-specific target amplification and detection in a variety of amplification reactions using only routine methods for production, screening and optimization.

In SDA, the bumper primers are not essential for species specificity, as they function to displace the downstream, species-specific amplification primers. It is required only that the bumper primers hybridize to the target upstream from the amplification primers so that when they are extended they will displace the amplification primer and its extension product. The particular sequence of the bumper primer is therefore generally not critical, and may be derived from any upstream target sequences which are sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence.

Amplification reactions employing the primers of the invention may incorporate thymine as taught by Walker, et al. (1992, *Nucl. Acids Res.* 20:1691–1696), or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product unamplifiable in subsequent amplification reactions. UDG may be inactivated by uracil DNA glycosylase inhibitor (UGI) prior to performing the subsequent amplification to prevent excision of dU in newly-formed amplification products.

SDA is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occurs concurrently in the reaction mix. This is in contrast to PCR, in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an α-thio deoxynucleoside triphosphate (α-thio dNTP), 3) nicking of a hemimodified double stranded restriction site, 4) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others which display the required nicking activity are suitable for use in conventional SDA. However, they are relatively thermolabile and lose activity above about 40° C.

Targets for amplification by SDA may be prepared by fragmenting larger nucleic acids by restriction with an endonuclease which does not cut the target sequence. However, it is generally preferred that target nucleic acids having selected restriction endonuclease recognition/cleavage sites for nicking in the SDA reaction be generated as described by Walker, et al. (1992, *Nucl. Acids Res.* 20:1691–1696) and in U.S. Pat. No. 5,270,184 (specifically incorporated herein by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced from the original target sequence template by extension of $B_1$ and $B_2$. The displaced, single stranded extension products of the amplification primers serve as targets for binding of the opposite amplification and bumper primer (e.g., the extension product of $S_1$ binds $S_2$ and $B_2$). The next iteration of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA iteration and are amplified.

To prevent cross-contamination of one SDA reaction by the amplification products of another, dUTP may be incorporated into SDA-amplified DNA in place of dTTP without inhibition of the amplification reaction. The uracil-modified nucleic acids may then be specifically recognized and inactivated by treatment with uracil DNA glycosylase (UDG). Therefore, if dUTP is incorporated into SDA-amplified DNA in a prior reaction, any subsequent SDA reactions can be treated with UDG prior to amplification of double stranded targets, and any dU containing DNA from previously amplified reactions will be rendered unamplifiable. The target DNA to be amplified in the subsequent reaction does not contain dU and will not be affected by the UDG treatment. UDG may then be inhibited by treatment with UGI prior to amplification of the target.

Alternatively, UDG may be heat-inactivated. In tSDA, the higher temperature of the reaction itself ($\leq 50°$ C.) can be used concurrently to inactivate UDG and amplify the target.

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. The polymerase must extend by adding nucleotides to a free 3'-OH. To optimize the SDA reaction, it is also desirable that the polymerase be highly processive to maximize the length of target sequence which can be amplified. Highly processive polymerases are capable of polymerizing new strands of significant length before dissociating and terminating synthesis of the extension product. Displacement activity is essential to the amplification reaction, as it makes the target available for synthesis of additional copies and generates the single stranded extension product to which a second amplification primer may hybridize in exponential amplification reactions. Nicking activity of the restriction enzyme is also of great importance, as it is nicking which perpetuates the reaction and allows subsequent rounds of target amplification to initiate.

tSDA is performed essentially as the conventional SDA described by Walker, et al. (1992, *Proc. Natl. Acad. Sci. USA* 89:392–396 and 1992, *Nucl. Acids Res.* 20:1691–1696), with substitution of the desired thermostable polymerase and thermostable restriction endonuclease. Of course, the temperature of the reaction will be adjusted to the higher temperature suitable for the substituted enzymes and the HincII restriction endonuclease recognition/cleavage site will be replaced by the appropriate restriction endonuclease recognition/cleavage site for the selected thermostable endonuclease. Also in contrast to Walker, et al., the practitioner may include the enzymes in the reaction mixture prior to the initial denaturation step if they are sufficiently stable at the denaturation temperature. Preferred restriction endonucleases for use in tSDA are BsrI, BstNI, BsmAI, BslI and BsoBI (New England BioLabs), and BstOI (Promega). The preferred thermophilic polymerases are Bca (Panvera) and Bst (New England Biolabs).

Homogeneous real time fluorescent tSDA is a modification of tSDA. It employs detector oligonucleotides to produce reduced fluorescence quenching in a target-dependent manner. The detector oligonucleotides contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, a restriction endonuclease recognition site (RERS) is present between the two dyes such that intermolecular base-pairing between the secondary structure and a complementary strand also renders the RERS double-stranded and cleavable by a restriction endonuclease. Cleavage by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ratio of fluorescence before and after unfolding) is monitored as an indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored. Cleavage of an oligonucleotide refers to breaking the phosphodiester bonds of both strands of a DNA duplex or breaking the phosphodiester bond of single-stranded DNA. This is in contrast to nicking, which refers to breaking the phosphodiester bond of only one of the two strands in a DNA duplex.

A detector oligonucleotide for homogeneous real time fluorescent tSDA may be an oligonucleotide which comprises both a single-stranded 5' or 3' section which hybridizes to the target sequence (the target binding sequence), as well as an intramolecularly base-paired secondary structure adjacent to the target binding sequence. In a preferred embodiment, as illustrated in FIG. 1, the detector oligonucleotide is a reporter probe that comprises a single-stranded 5' or 3' section that does not hybridize to the target sequence. Rather, the single-stranded 5' or 3' section hybridizes to the complement of the signal primer adapter sequence (the adapter-complement binding sequence). A further characteristic of the reporter probe is that this hybridizing section is adjacent to an intramolecularly base-paired secondary structure. The detector oligonucleotides of the invention further comprise a donor/acceptor dye pair linked to the detector oligonucleotide such that donor fluorescence is quenched when the secondary structure is intramolecularly base-paired and unfolding or linearization of the secondary structure results in a decrease in fluorescence quenching.

The detector oligonucleotides of the invention for homogeneous real time fluorescent tSDA comprise a sequence which forms an intramolecularly base-paired secondary structure under the selected reaction conditions for primer extension or hybridization. In one embodiment, the secondary structure may be positioned adjacent to the target binding sequence of the detector oligonucleotide so that at least a portion of the target binding sequence forms a single-stranded 3' or 5' tail. In a preferred embodiment, as illustrated in FIG. 1, the secondary structure is positioned adjacent to the adapter-complement binding sequence of the reporter probe detector oligonucleotide so that at least a portion of the adapter-complement binding sequence forms a single-stranded 3' or 5' tail. As used herein, the term "adjacent to the target binding sequence" or "adjacent to the adapter-complement binding sequence" means that all or part of the target/adapter-complement binding sequence is left single-stranded in a 5' or 3' tail which is available for hybridization to the target/adapter-complement. That is, the secondary structure does not comprise the entire target/adapter-complement binding sequence. A portion of the target/adapter-complement binding sequence may be involved in the intramolecular base-pairing in the secondary structure, it may include all or part of a first sequence involved in intramolecular base-pairing in the secondary structure but preferably does not extend into its complementary sequence. For example, if the secondary structure is a stem-loop structure (e.g., a "hairpin") and the target/adapter-complement binding sequence of the detector oligonucleotide is present as a single-stranded 3' tail, the target/adapter-complement binding sequence may also extend through all or part of the first arm of the stem and, optionally, through all or part of the loop. However, the target/adapter-complement binding sequence preferably does not extend into the second arm of the sequence involved in stem intramolecular base-pairing. That is, it is desirable to avoid having both sequences involved in intramolecular base-pairing in a secondary structure capable of hybridizing to the target/adapter-complement. Mismatches in the intramolecularly base-paired portion of the detector oligonucleotide secondary structure may reduce the magnitude of the change in fluorescence in the presence of target but are acceptable if assay sensitivity is not a concern. Mismatches in the target/adapter-complement binding sequence of the single-stranded tail are also acceptable but may similarly reduce assay sensitivity and/or specificity. However, it is a feature of the present invention that perfect base-pairing in both the secondary structure and the target/adapter-complement binding sequence do not compromise the reaction. Perfect matches in the sequences involved in hybridization improve assay specificity without negative effects on reaction kinetics.

When added to the amplification reaction, the detector oligonucleotide reporter probe of the invention is converted to double-stranded form by hybridization and extension as illustrated in FIG. 1. Strand displacement by the polymerase also unfolds or linearizes the secondary structure and converts it to double-stranded from by synthesis of a complementary strand. The RERS, if present, also becomes double-stranded and cleavable by the restriction endonuclease. As the secondary structure is unfolded or linearized by the strand displacing activity of the polymerase, the distance between the donor and acceptor dye is increased, thereby reducing quenching of donor fluorescence. The associated change in fluorescence of either the donor or acceptor dye may be monitored or detected as an indication of amplification of the target sequence. Cleavage of the RERS generally further increases the magnitude of the change in fluorescence by producing two separate fragments of the double-stranded secondary amplification product, each having one of the two dyes linked to it. These fragments are free to diffuse in the reaction solution, further increasing the distance between the dyes of the donor/acceptor pair. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair may also be monitored. A change in fluorescence intensity of the donor or acceptor may also be detected as a change in a ratio of donor and/or acceptor fluorescence intensities. For example, a change in fluorescence intensity may be detected as; a) an increase in the ratio of donor fluorophore fluorescence after linearizing or unfolding the secondary structure and donor fluorophore fluorescence in the detector oligonucleotide prior to linearizing or unfolding, or b) as a decrease in the ratio of acceptor dye fluorescence after linearizing or unfolding and acceptor dye fluorescence in the detector oligonucleotide prior to linearizing or unfolding.

It will be apparent that, in addition to SDA, the detector oligonucleotides of the invention may be adapted for use in the detection of amplicons in other primer extension amplification methods (e.g., PCR, 3SR, TAS or NASBA). For example, the methods may be adapted for use in PCR by using PCR amplification primers and a strand displacing DNA polymerase which lacks 5'→3' exonuclease activity (e.g., Sequencing Grade Taq from Promega or exo⁻ Vent or exo⁻ Deep Vent from New England BioLabs) in the PCR. The signal primers hybridize to the target at least partially downstream from the PCR amplification primers, are displaced and are rendered double-stranded essentially as described for SDA. In PCR any RERS may optionally be selected for use in the detector oligonucleotide, as there are typically no modified deoxynucleoside triphosphates present which might induce nicking rather than cleavage of the RERS. As thermocycling is a feature of amplification by PCR, the restriction endonuclease is preferably added at low temperature after the final cycle of primer annealing and extension for end-point detection of amplification. However, a thermophilic restriction endonuclease that remains active through the high temperature phases of the PCR reaction could be present during amplification to provide a real-time assay. As in SDA systems, separation of the dye pair reduces fluorescence quenching, with a change in a fluorescence parameter such as intensity serving as an indication of target amplification.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format may be used to provide semiquantitative or quantitative information about the initial amount of target present. For example, the rate at which fluorescence intensity changes during the unfolding or linearizing reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required to reach a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as are known in the art (e.g., U.S. Pat. No. 5,928,907, U.S. patent application Ser. No. 09/196,123, filed Nov. 20, 1998, and U.S. patent application Ser. No. 09/574,031, filed May, 19, 2000, all of which are specifically incorporated herein by reference) may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample that may interfere with detection of the signal or other aspects of the assay. An example of a solid phase system that can be used is an array format known in the art.

EXAMPLES

The following Examples illustrate specific embodiments of the invention described herein. As would be apparent to skilled artisans, various changes and modifications are possible, and are contemplated within the scope of the invention described.

Example 1

Analytical Sensitivity

Amplification reactions were conducted in the presence of 500, 250, 100, 50, 10 and zero copies of a cloned plasmid containing the promoter of the pertussis toxin gene. The amplification reactions were conducted at 52° C. in buffer containing final concentrations of the following components: 30 mM potassium phosphate, 13% Glycerol, 13% dimethylsulfoxide (DMSO), 75 mM bicine, 50 mM potassium hydroxide, 5 mM magnesium acetate, 700 ng human placental DNA, 100 µg acetylated bovine serum albumin, 100 nM upstream primer (SEQ ID NO:1), 500 nM downstream primer (SEQ ID NO:2), 50 nM bumper primers (SEQ ID NO: 4 and SEQ ID NO: 6), 250 nM signal primer (SEQ ID NO:9), 500 nM reporter probe (SEQ ID NO:11), 0.1 mM dATP, 0.1mM dGTP, 0.1 mM dTTP, 0.5 mM 2'-Deoxycytidine 5'-O-(1-Thiotriphosphate) s-isomer, and approximately 4 units Bst polymerase and 24 units BsoB1.

In brief, target DNA was denatured for 5 minutes at 95° C. and cooled to room temperature prior to addition to a buffer containing the primers and bumpers. Incubation was continued at room temperature for 20 minutes, followed by incubation at 70° C. for 10 minutes to minimize potential false priming. Amplification was then initiated at 52° C. by transfer of a fixed volume of the priming mix to microtiter wells containing the amplification enzymes. Amplification was carried out for 1 hour at a constant temperature of 52° C. Specific amplification products were detected by monitoring the change in fluorescence intensity associated with the hybridization of reporter probe (SEQ ID NO:11) to the complement of the signal primer SEQ ID NO:9, the subsequent extension of the signal primer complement and cleavage of the resultant double stranded product. The limit of detection (calculated to be the target level that predicts a positivity rate of 95%) was between 60 and 145 copies per reaction.

Example 2
Evaluation of Primer Specificity

Primer specificity was evaluated using SEQ ID NO:1, SEQ ID NO:2, SEQ ID NO:4, SEQ ID NO:6, SEQ ID NO:9 and SEQ ID NO:11, as described above. Eleven strains of *B. pertussis* were tested at approximately $1 \times 10^6$ genomic equivalents per reaction (Table 2). Ten of eleven strains tested positive. ATCC strain #13600 was negative by both SDA and PCR for different regions of the pertussis toxin promoter gene. Since strain #13600 was described as mixed culture on the strain specification sheet from ATCC, it is likely that the level of *B. pertussis* was below the limit of detection of either amplification method.

TABLE 2

| ptx Specificity Panel Species | ATCC Strain # |
|---|---|
| B. pertussis | 9797 |
| B. pertussis | 8478 |
| B. pertussis | 10380 |
| B. pertussis | 11615 |
| B. pertussis | 12743 |
| B. pertussis | 13600* |
| B. pertussis | 53894 |
| B. pertussis | 51445 |
| B. pertussis | 9832 |
| B. pertussis | 12742 |
| B. pertussis | 9340 |

*Negative by SDA for ptx target sequence. Described as mixed culture by ATCC.

Example 3
Evaluation of Cross-Reactivity

Cross-reactivity was evaluated using the primers and reaction conditions described in Example 2. Organisms other than *B. pertussis* were tested with $1 \times 10^6$ genomic equivalents per reaction. Negative results were obtained with all 49 organisms tested (Table 3).

TABLE 3

| ptx Cross-Reactivity Panel | |
|---|---|
| Species | ATCC Strain |
| Acinetobacter calcoaceticus | 13339 |
| Aeromonas hydrophila | 7966 |
| Alcaligenes faecalis | 8750 |
| Blastomyces dermatitidis | 4292 |
| Bordetella bronchiseptica | 10580 |
| Bordetella hinzii | 51783 |

TABLE 3-continued

| ptx Cross-Reactivity Panel | |
|---|---|
| Species | ATCC Strain |
| Bordetella holmesii | 51541 |
| Bordetella parapertussis | 15311 |
| Branhamella catarrhalis | 25285 |
| Candida albicans | 44808 |
| Citrobacter freundii | 8090 |
| Coccidioides immitis | 7366 |
| Corynebacterium diphtheriae | 11913 |
| Corynebacterium jeikeium | 43734 |
| Cryptococcus neoformans | 36556 |
| Eikenella corrodens | 23834 |
| Enterobacter aerogenes | 13048 |
| Enterobacter cloacae | 13047 |
| Enterococcus faecalis | 29212 |
| Enterococcus faecium | 19434 |
| Escherichia coli | 11775 |
| Fusobacterium nucleatum | 25586 |
| Group B Streptococcus | 12386 |
| Haemophilus influenzae | 33533 |
| Haemophilus parainfluenzae | 7901 |
| Histoplasma capsulatum | 12700 |
| Klebsiella pneumoniae ssp. ozaenae type4 | 11296 |
| Klebsiella pneumoniae ssp. Pneumoniae | 13883 |
| Lactobacillus acidophilus | 4356 |
| Legionella micdadei | 33204 |
| Legionella pneumophila | 33152 |
| Moraxella osloensis | 19976 |
| Neisseria gonorrhoeae | 19424 |
| Neisseria mucosa | 19696 |
| Peptostreptococcus anaerobius | 27337 |
| Prevotella oralis (Bacteroides oralis) | 33269 |
| Pseudomonas aeruginosa | 27853 |
| Pseudomonas pertucinogena | 190 |
| Salmonella choleraesuis serotype enteritidis | 13076 |
| Salmonella choleraesuis serotype typhi | 19430 |
| Serratia marcescens | 8100 |
| Staphylococcus aureus, protein A-producing | 12598 |
| Staphylococcus aureus, non-protein A-producing | 25923 |
| Staphylococcus epidermidis | E155 |
| Strenotrophomonas maltophilia | 13637 |
| Streptococcus mutans | 25175 |
| Streptococcus pneumoniae | 6303 |
| Streptococcus pyogenes | 19615 |
| Veillonella parvula | 10790 |

While the invention has been described with some specificity, modifications apparent to those of ordinary skill in the art may be made without departing from the scope of the invention. Various features of the invention are set forth in the following claims.

What is claimed is:

1. An oligonucleotide consisting of a target binding sequence selected from the group consisting of the target binding sequences of ptxL9 (SEQ ID NO:1), ptxR10 (SEQ ID NO:2) and ptxR11 (SEQ ID NO:3) and optionally, a sequence required for an amplification reaction.

2. The oligonucleotide of claim 1 wherein the sequence required for the amplification reaction is a restriction endonuclease recognition site which is nickable by a restriction endonuclease.

3. The oligonucleotide of claim 2 selected from the group consisting of ptxL9 (SEQ ID NO:1), ptxR10 (SEQ ID NO:2) and ptxR11 (SEQ ID NO:3).

4. An oligonucleotide selected from the group consisting of ptxLB2 (SEQ ID NO:4), ptxRB3 (SEQ ID NO:5) and ptxRB4 (SEQ ID:6).

5. An oligonucleotide selected from the group consisting of ptxA1 (SEQ ID NO:7), a nucleic acid complementary to SEQ ID NO:7, ptxA3 (SEQ ID NO:8), a nucleic acid complementary to SEQ ID NO:8, ptxA4 (SEQ ID NO:9), a nucleic acid complementary to SEQ ID NO:9, ptxA5 (SEQ ID NO:10) and a nucleic acid complementary to SEQ ID NO:10.

6. The oligonucleotide of claim 5 wherein said oligonucleotide comprises an indirectly detectable marker.

7. The oligonucleotide of claim 6 wherein said indirectly detectable marker is an adapter sequence.

8. A pair of amplification primers comprising:

a) a first primer consisting of a target binding sequence of ptxL9 (SEQ ID NO:1) and, optionally, a sequence required for an amplification reaction, and;

b) a second primer consisting of a target binding sequence selected from the group consisting of the target binding sequences of ptxR10 (SEQ ID NO:2) and ptxR11 (SEQ ID NO:3), and, optionally, a sequence required for an amplification reaction.

9. The pair of amplification primers of claim 8 wherein the sequence required for the amplification reaction is a restriction endonuclease recognition site which is nickable by a restriction endonuclease.

10. The pair of amplification primers of claim 9 wherein said first primer is ptxL9 (SEQ ID NO:1) and said second primer is selected from the group consisting of ptxR10 (SEQ ID NO:2) and ptxR11 (SEQ ID NO:3).

11. The pair of amplification primers of claim 9 wherein said first primer is ptxL9 (SEQ ID NO:1) and said second primer is ptxR10 (SEQ ID NO:2).

12. A kit comprising:

a) one primer consisting of ptxL9 (SEQ ID NO:1), b) one or more primers selected from the group consisting of ptxR10 (SEQ ID NO:2) and ptxR11 (SEQ ID NO:3), c) one or more bumpers selected from the group consisting of ptxLB2 (SEQ ID NO:4), ptxRB3 (SEQ ID NO:5) and ptxRB4 (SEQ ID NO:6).

d) one or more signal primers selected from the group consisting of ptxA1 (SEQ ID NO:7), a nucleic acid complementary to SEQ ID NO:7, ptxA3 (SEQ ID NO:8), a nucleic acid complementary to SEQ ID NO:8, ptxA4 (SEQ ID NO:9), a nucleic acid complementary to SEQ ID NO:9, ptxA5 (SEQ ID NO:10), and a nucleic acid complementary to SEQ ID NO:10.

13. The kit of claim 12 wherein said one or more signal primers comprises an indirectly detectable marker.

14. The kit of claim 13 wherein said indirectly detectable marker is an adapter sequence.

15. The kit of claim 14 further comprising a reporter probe of SEQ ID NO:11.

16. The kit of claim 12 further comprising:

e) a pair of primers specific for the amplification of a nucleic acid sequence specific for *Legionella pneumophila;* f) a pair of primers specific for the amplification of a nucleic acid sequence specific for *Mycoplasma pneumoniae*; and g) a pair of primers specific for the amplification of a nucleic acid sequence indicative of a chlamydial infection.

17. A method for detecting the presence or absence of *Bordetella pertussis* organisms in a sample, said method comprising:

a) treating said sample using a pair of nucleic acid primers in a nucleic acid amplification reaction wherein a first primer consists of ptxL9 (SEQ ID NO:1) and a second primer consisting of ptxR10 (SEQ ID NO:2), and b) detecting any amplified nucleic acid product, wherein detection of amplified product indicates presence of *Bordetella pertussis* organisms.

18. The method of claim 17 wherein said nucleic acid amplification reaction is a Strand Displacement Amplification (SDA) reaction.

19. The method of claim 18 wherein said SDA reaction utilizes ptxLB2 (SEQ ID NO:4) and ptxRB4 (SEQ ID NO:6) as bumpers.

20. The method of claim 17 wherein detecting said amplified nucleic acid product is conducted by hybridizing said amplified nucleic acid product with a signal primer consisting of ptxA4 (SEQ ID NO:9).

21. The method of claim 18 wherein said SDA reaction is a thermophilic Strand Displacement Amplification (tSDA) reaction.

22. The method of claim 21 wherein said tSDA reaction is a homogeneous fluorescent real time tSDA reaction.

23. A method for amplifying a target nucleic acid sequence of a *Bordetella pertussis* organism comprising:

a) hybridizing to the nucleic acid i) a first amplification primer consisting of a target binding sequence of ptxL9 (SEQ ID NO:1) and, optionally, a sequence required for an amplification reaction, and ii) a second amplification primer consisting of a target binding sequence of ptxR10 (SEQ ID NO:2), and, optionally, a sequence required for the amplification reaction, and;

b) extending the hybridized first and second amplification primers on the target nucleic acid sequence whereby the target nucleic acid sequence is amplified.

24. The method of claim 23 further comprising indirectly detecting the amplified target nucleic acid by hybridization to a signal primer.

25. The method of claim 24 wherein the signal primer consists of ptxA4 (SEQ ID NO:9).

26. The method of claim 23 wherein the sequence required for the amplification reaction is a recognition site for a restriction endonuclease that is nicked by the restriction endonuclease during Strand Displacement Amplification.

27. The method of claim 23 wherein the hybridized first and second amplification primers are displaced from the target nucleic acid by extension of a first bumper primer consisting of ptxLB2 (SEQ ID NO:4) and a second bumper primer consisting of ptxRB4 (SEQ ID NO:6).

28. The method of claim 23 wherein the target nucleic acid is amplified by the Polymerase Chain Reaction.

29. The method of claim 26 wherein said SDA reaction is a thermophilic Strand Displacement Amplification (tSDA) reaction.

30. The method of claim 29 wherein said tSDA reaction is a homogeneous fluorescent real time tSDA reaction.

* * * * *

SEQUENCE LISTING

<160> NUMBER OF SEQ ID NOS: 11

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence:Upstream
      primer for SDA of Bordetella pertussis.

<400> SEQUENCE: 1
cgattccgct ccagacttct cgggccgcat acgtgttg                    38

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:Downstream
      primer for SDA of Bordetella pertussis.

<400> SEQUENCE: 2
accgcatcga ttgcatgtct cgggtgccgt gttggattg                   39

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence:Downstream
      primer for SDA of Bordetella pertussis.

<400> SEQUENCE: 3
accgcatcga ttgcatgtct cgggcgccgt gttggattg                   39

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence:Upstream
      bumper for SDA of Bordetella pertussis.

<400> SEQUENCE: 4
cggccggcac cat                                               13

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence:Downstream
      bumper for SDA for Bordetella pertussis.

<400> SEQUENCE: 5
cgaaggagcg ttca                                              14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence:Downstream
      bumper for SDA for Bordetella pertussis.

<400> SEQUENCE: 6
accatcgcgc gact                                                           14

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence:Signal
      primer for SDA for Bordetella pertussis.

<400> SEQUENCE: 7
acgttagcca ccatacggat cgtcgtacta aaccctcgat tcttc               45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence:Signal
      primer for SDA for Bordetella pertussis.

<400> SEQUENCE: 8
acgttagcca ccatacggat gattcgtcgt actaaaccct cgatt               45

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence:Signal
      primer for SDA for Bordetella pertussis.

<400> SEQUENCE: 9
acgttagcca ccatacggat gattcgtcgt acaaaccct cgatt                45

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence:Signal
      primer for SDA for Bordetella pertussis.

<400> SEQUENCE: 10
acgttagcca ccatacggat ctgcagatgc gtcgtacaaa accctcgatt           50

<210> SEQ ID NO 11
<211> LENGTH: 35
<212> TYPE: DNA
<213> ORGANISM: Artificial Sequence
<220> FEATURE:
<221> NAME/KEY: misc_feature
<222> LOCATION: (1)
<223> OTHER INFORMATION: This base is modified by attachment of
      fluorescein.
<221> NAME/KEY: misc_feature
<222> LOCATION: (15)
<223> OTHER INFORMATION: This base is modified by attachment of dabcyl.
<223> OTHER INFORMATION: Description of Artificial Sequence:Reporter
      probe sequence for SDA for Bordetella pertussis.

<400> SEQUENCE: 11
tagtgcccga gcactacgtt agccaccata cggat                          35